US005110491A

United States Patent [19]

Derosa et al.

[11] Patent Number: 5,110,491

[45] Date of Patent: May 5, 1992

[54] OLIGOMERIC LUBRICANT ADDITIVE DESIGNED TO ENHANCE ANTIOXIDANCY AND CORROSION RESISTANCE IN RAILWAY DIESEL CRANKCASE LUBRICANTS

[75] Inventors: Thomas F. Derosa, Passaic, N.J.; Rodney L. Sung, Fishkill, N.Y.; Benjamin J. Kaufman, Hopewell, N.Y.; Ronald L. O'Rourke, Hyde Park, N.Y.

[73] Assignee: Texaco Inc., White Plains, N.Y.

[21] Appl. No.: 688,801

[22] Filed: Apr. 22, 1991

[51] Int. Cl.[5] ................ C10M 141/06; C10M 141/08; C07D 285/14

[52] U.S. Cl. .................................. 252/47.5; 548/142; 525/382; 525/349

[58] Field of Search ............... 252/47.5; 525/382, 349; 548/142

[56] References Cited

U.S. PATENT DOCUMENTS

| | | | |
|---|---|---|---|
| 3,914,241 | 10/1975 | Elliott et al. | 548/142 |
| 5,055,584 | 10/1991 | Karol | 548/142 |
| 4,089,794 | 5/1978 | Engel et al. | 252/51.5 A |
| 4,144,034 | 3/1979 | Cummings | 44/407 |
| 4,193,882 | 3/1980 | Gemmill, Jr. | 252/47.5 |
| 4,357,250 | 11/1982 | Hayashi | 252/51.5 A |
| 4,562,260 | 12/1985 | McDaniel, Jr. et al. | 548/142 |
| 4,659,337 | 4/1987 | Sung | 44/407 |
| 4,904,403 | 2/1990 | Karol | 252/47.5 |
| 5,013,469 | 5/1991 | DeRosa et al. | 252/47.5 |

*Primary Examiner*—Prince Willis, Jr.
*Assistant Examiner*—J. Silbermann
*Attorney, Agent, or Firm*—Robert A. Kulason; James J. O'Loughlin; Vincent A. Mallare

[57] ABSTRACT

A railway diesel crankcase lubricant composition comprising a major portion of a diesel lubricating oil and a minor amount of, as an oxidation and corrosion inhibiting agent, a condensate product prepared by the process comprising:

(a) reacting a dibasic acid anhydride, separately, with:
  (i) a oligomeric isobutylene, and
  (ii) 2,5-dimercapto-1,3,4,-thiadiazole, to produce, respectively, oligomeric(isobutylene-g-succinic anhydride) and 2-thio-(5-mercapto-1,3,4-thiadiazole) succinic anhydride;

(b) reacting both of the succinic anhydrides with pentamethylenediamine to produce the [2-thio-(5-mercapto-1,3,4-thiadiazole)]-[oligomeric(isobutylene-g-succinic)]-pentamethylenetetraamine-bis succinimide product; and (c) recovering the bis-succinimide product.

5 Claims, No Drawings

OLIGOMERIC LUBRICANT ADDITIVE DESIGNED TO ENHANCE ANTIOXIDANCY AND CORROSION RESISTANCE IN RAILWAY DIESEL CRANKCASE LUBRICANTS

BACKGROUND OF THE INVENTION

This invention relates to a functionalized oligomeric lubricant additive which imparts enhanced anti-oxidancy and corrosion resistance upon dissolution in lubricating oils. More specifically, this invention relates to railway diesel lubricants and, more particularly, to diesel fuels containing anti-corrosion and anti-oxidation additives for improving the corrosion inhibition and anti-oxidation properties in motor fuels.

The past ten years have seen a dramatic increase in the cost of diesel fuel. For example, the price of marine diesel fuel has increased from approximately $11 a metric ton to a high of about $200 a metric ton. Additionally, a similar increase in fuel cost has been experienced by the railroad industry. The net effect of these price increases have resulted in the cost of fuel being the largest single operating expense for owners of any diesel fleet of vehicles. To try to obtain some relief, railroads have embarked on a program of mixing poorer grade fuels (such as marine residual) with regular D-2 diesel fuel. While they do realize a savings from this mixed fuel operation, performance problems arise, such as increased corrosion and poorer oxidative stability. The commitment to this mixed-fuel approach is reflected in General Electric's spending $20 million and while General Motors (EMD) also exerting a similar type of effort to determine optimum performance using mixed fuels.

Thus, the primary objective of this invention is to provide a novel railway diesel crankcase lubricating additive that enhances the oxidative corrosion resistant properties of these mixed fuels or oils.

DISCLOSURE STATEMENT

U.S. Pat. No. 3,773,479 discloses the use of the reaction product of maleic anhydride and alkyl or alkenyl amines as carburetor detergents, corrosive inhibitor, and as anti-icing additive in motor oils.

U.S. Pat. No. 4,089,794 discloses how the incorporation of ethylenically unsaturated carboxylic acid materials that have been post-reacted with a polyamine, polyol, or a hydroxylamine become effective as sludge control additive for lubricants.

U.S. Pat. No. 4,144,034 discloses the use of the reaction product of maleic anhydride and certain alkyl-alkylene diamines as a corrosion inhibitor and a carburetor detergent additive and corrosion inhibitor in motor fuels.

U.S. Pat. No. 4,290,778 discloses the use of the reaction product of an alkoxyalkylene diamine and maleic anhydride as a corrosion inhibitor and carburetor detergent additive in motor fuels.

U.S. Pat. No. 4,340,689 discloses a process for chemically grafting a functional organic group onto an ethylene-propylene copolymer or an ethylene-propylene-diene terpolymer.

U.S. Pat. No. 4,357,250 discloses a method of incorporating ethylenically unsaturated carboxylic acid or acid anhydrides onto oligomeric or U.S. Pat. No. 4,904,403 disclosed a method incorporating 1,3,4-thiadiazole onto an oligomeric or polymeric substrate as an anti-wear additive in lubricating oils.

The disclosures in the foregoing patents which relate to anti-oxidancy and anti-corrosion for lubricating oils, namely U.S. Pat. Nos. 3,773,479; 4,089,794; 4,144,034; 4,290,778; 4,340,689; 4,357,250; and 4,904,403 are incorporated herein by reference.

SUMMARY OF THE INVENTION

According to the present invention, it has been discovered that the dissolution of the imidization reaction product of oligomeric polyisobutylene containing one or more succinic anhydride or succinic acid moieties imidized with a polyalkylamine containing a diathiazole nucleus in oil causes two measurable and extremely desirable effect to the oil. Both these effects become apparent during engine operating conditions. The first effect pertains to enhanced oil oxidative resistance. This effect may be observed by measuring the oil viscosity. The second effect pertains to enhanced oil corrosion resistance. This effect may be observed by measuring the concentration of dissolved metallic ions such as lead, iron, copper, and tin contained in the oil.

The present invention provides a railway diesel crankcase lubricant composition comprising a major portion of a diesel lubricating oil and a minor amount of an oxidation and corrosion inhibiting agent. This condensate reaction product is prepared by the process comprising:

(a) reacting a dibasic acid anhydride of the formula

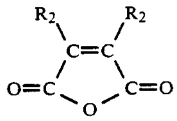

where $R_1$ and $R_2$ is hydrogen or a ($C_1$–$C_{10}$) linear or branched alkyl or cyclic alkyl group, separately, with (i) a oligomeric isobutylene represented the formula:

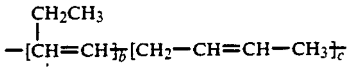

where the sum of the repeat units, b and c, are limited to the range of 10 to 500 so that the material has a corresponding molecular weight range from about 500 amu to 15,000 amu to produce oligomeric (isobutylene -g-succinic anhydride) and (ii) 2,5-dimercapto-1,3,4,-thiodiazole represented by the formula:

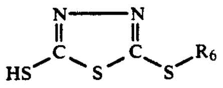

where $R_6$ is hydrogen or a ($C_1$–$C_{10}$) linear or branched aliphatic hydrocarbon to produce 2-thio-(5-mercapto-1,3,4-thiadiazole) succinic anhydride;

(b) reacting the oligomeric (isobutylene-g-succinic anhydride) and the thiadiazole succinic anhydride with pentamethylene-diamine to produce the product of [2-thio-(5-mercapto-1,3,4-thiadiazole)] -[oligomeric (isobutylene g-succinic)] - pentamethylene- bis succinimide; and (c) recovering said product bis-succinimide

DETAILED DESCRIPTION OF THE INVENTION

The present invention deals with the scenario where diesel fuel (D-2) is extended with diesel residual fuel, as proposed by the railroad industry. As a result, railway diesel oil (RDO) will be subjected to more severe conditions during operation. We have simulated the scenario wherein RDO is contaminated with a given amount of marine diesel residual fuel. We believe this to be a realistic test since during the normal engine operation D-2 gets into the diesel crankcase. Finally, the Union Pacific Oxidation Test (UPOT) was used to evaluate the effectiveness of the experimental additives impeding corrosion and oxidative thickening of the RDO.

The pentamethylenediamine may be substituted with a N-alkyl alkyene diamine having the structural formula:

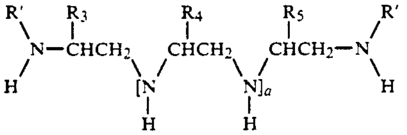

where R' is a hydrogen or a ($C_1$ to $C_{10}$) hydrocarbon group and $R_3$, $R_4$ and $R_5$ is hydrogen or a ($C_1$ to $C_{10}$) hydrocarbon group, is an integer between 0 and 7.

The heterocyclic 1,3,4-thiadiazole nucleus of the present invention is structurally represented as:

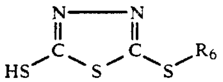

where $R_6$ is hydrogen or a ($C_1$–$C_{10}$) linear or branched aliphatic alcohol or amine.

The dibasic acid or anhydride os this invention may be represented by the structural formula:

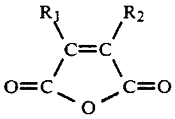

where $R_1$ and $R_2$ is hydrogen or a ($C_1$–$C_{10}$) linear or branched alkyl or cyclic alkyl structure. Dibasic anhydrides amenable to this process include maleic anhydride; alpha-methyl maleic anhydride; alpha,beta dimethyl maleic anhydride; alpha, beta dimethyl maleic anhydride; alpha-ethyl maleic anhydride; 2alpha,beta-di-n-propyl maleic anhydride; alpha-n-hexyl maleic anhydride; alpha, beta-di-n-hexyl maleic anhydride; alpha-n-nonyl nonyl maleic anhydride; alpha, beta-di-n-octyl maleic anhydride; alpha, beta-di-n-nonyl maleic anhydride.

The preferred dibasic acid anhydride is maleic anhydride. The polyalkylated alkylimide of 1,3,4-thiadiazole wherein a is 1, the sum of b and c is approximately 25, and where $R_1$, $R_2$, $R_3$, $R_4$, $R_5$ and $R_6$ are hydrogen is available from R. T. Vanderbilt Company, Inc., of Norwalk, Conn. under the Tradename of OCD-077.

This invention is also directed to a marine crankcase lubricant composition containing the prescribed polyalkylated alkylimide of 1,3,4-thiadiazole which exhibit substantially reduced oxidation and corrosion tendencies.

The reaction product of this invention is prepared by a multistep process. Initially, oligomeric butylene represented by the formula,

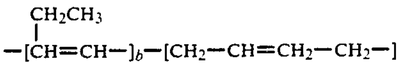

viz., oligomerized 1,3-butadiene containing a mixed and random 1,2- and 1,4- repeat unit where the sum of the repeat units, b and c, are limited to the range of 10 to 50 so that the material has a corresponding molecular weight range of from 500 amu to 15,000 amu, is reacted with an ethylenically unsaturated acid or, more preferably, an acid anhydride.

The preferred method of incorporation of maleic anhydride onto the oligomeric polyisobutylene is through the "ene" reaction. During this preferred method, oligomeric isobutylene and approximately 0.05 wt% to 5.00 wt% maleic anhydride are heated in the presence or absence of an inert reaction solvent. Heating is continued for a sufficient time to ensure that at least 95 wt% of the anhydride becomes chemically incorporated onto the oligomeric substrate, typically 0.5 hrs to 3.0 hrs. The molecular weight of the oligomeric substrate may range from about 300 amu to about 15,000 amu. In no case, however, will the molecular weight of the polymeric substrate influence the ene reaction kinetics.

Examples of oligomeric olefins amenable to the ene reaction include those derived from alpha-olefin monomers such as isoprene, isobutene, 2-methyl-n-heptene, 2,4-dimethyl-nheptene, and the like.

The preferred oligomeric olefin is oligomeric butylene, however, and is available from the Amoco Chemical Company under the tradename ACTIPOL.

These above ene reaction intermediates are imidized using the imidization reaction product of an N-alkyl-alklene diamine, and maleic anhydride and 2,5-dimercapto-1,3,4-thiadiazole.

The amines which may be employed in the present process include polyamines, preferably diamines, which bear at least two primary amine-NH2 groups and at least one amine groups. The latter may be mono- or di-substituted by linear or branched aliphatic hydrocarbons.

The preferred amine has the structural formula:

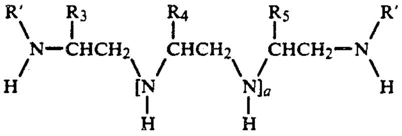

wherein R' is hydrogen or a ($C_1$–$C_{10}$) hydrocarbon group and $R_3$, $R_4$, and $R_5$ each are hydrogen or a ($C_1$–$C_{10}$) hydrocarbon group, and a is an integer between 0 and 7.

The preferred N-primary alkylalkylkene diamines include tetra-ethylenediamine, pentaethylenediamine, and hexaethylenediamine.

In accordance with the present invention, the process comprises the addition to the hydrocarbon fuel, of a minor deposit-inhibiting amount of, as a deposit-inhibiting additive, a reaction product of (a) an oligomeric olefin, (b) maleic anhydride, and (c) an N-alkyl-alkylene diamine and a 1,3,4-thiadiazole.

The synthetic process proceeds in three Phases and is summarized below, and then illustrated by a flow diagram.

Phase I

In this initial synthetic phase, maleic anhydride (A) is reacted with oligomeric olefins (B) to form the succinic anhydride adduct (C).

Phase II

In this second phase, equimolar amounts of maleic anhydride (A) and 2,5-dimercapto-1,3,4-thiadiazole (D) are reacted together to form a second succinic anhydride adduct (E).

Phase III.

This is the coupling phase. In this phase reaction intermediates (C) and (E) are imidized using an N-alkyl alkyene diamine (F) to form a mixed imidization product (G).

FLOW DIAGRAM

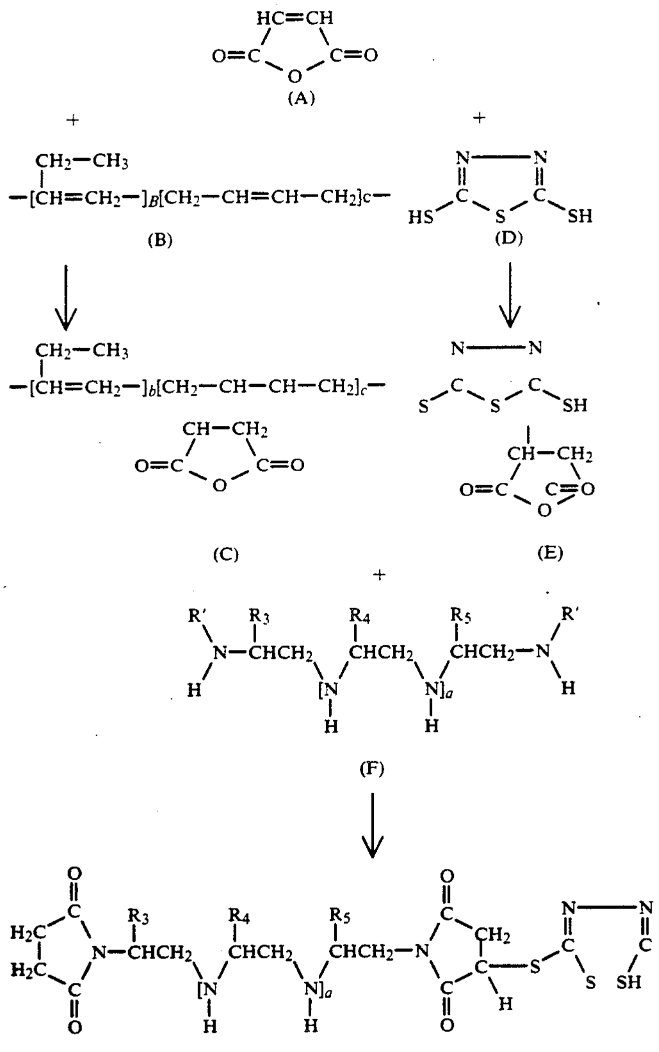

(A) (B) (D) (C) (E) (F)

(G)

The following examples are provided to illustrate the preferred method of preparing the present reaction product and the effectiveness of the product in railway diesel crankcase lubricants. It will be understood that the following examples are merely illustrative and are not meant to limit in any way the invention.

EXAMPLE I

Preparation Of Oligomeric(Isobutylene-g-Succinic Anhydride)

In a preferred method for preparing the reaction product, maleic anhydride and oligomericisobutylene with an Mn = 900 are mixed together in toluene and heated to solvent reflux temperature for 5 hours under an inert and anhydrous atmosphere, such as nitrogen. The reagent weight ratios are chosen so that 0.10 wt % to 0.50 wt% of maleic anhydride is grafted to the oligomeric substrate to produce the oligomeric (isobutylene-q-succinic anhydride).

EXAMPLE II

Preparation Of 2-Thio-(5-Mercapto-1,3,4-Thiadiazole)-Succinic Anhydride

In the preferred method for preparing this product, equimolar amounts of 2,5 dimercapto-I,3,4-diathiazole and maleic anhydride are dissolved in I:1 v/v toluene and tetrahydrofuran and heated to reflux temperature for approximately 6 hours under a protective blanket of nitrogen. pressure and a yellow resinous material isolated to form 2-thio-(5-mercapto-1,3,4-thiadiozole)-succinic anhydride.

EXAMPLE III

Coupling Product Of 2-Thio-(5-Mercapto-1,3,4-Thiadiazole)Succinic Anhydride And Olioomeric(Isobutylene-g-Succinic Anhydride) Using Pentamethylenehexaamine 2-thio-(5-mercapto-1,3,4-thiadiazole)-succinic anhydride and oligomeric(isobutylene-g-succinic anhydride) are dissolved in toluene so that a 1:1 molar ratio of reagents is obtained. Moreover, the solute concentration ideally remains under 50 wt % to avoid agitation problems associated with high solution viscosity. Sufficient pentamethylenehexaamine is added to the mixture as to cause complete imidization of all anhydrides present. The reaction mixture is heated to reflux temperature for 10 hours under an inert atmosphere to yield the coupling product of the succinic anhydrides of Examples I and II, i.e., [2-thio-(5-mercapto-1,3,4-thiadiazole)] - oligomeric (isobutylene-q-succinic)]-pentamethylenetetraamine-bissuccinimide.

The preferred components of the railway diesel crankcase lubricating oil composition of the present invention are those which are effective in a range of from about 0.1 to about 5 wt % based on the total lubricating oil composition. However, it is economically preferred to employ from about 0.5 to 2.0 wt % of the derivative based on the weight of the lubricating oil with the most preferred concentration being between 0.75 to about 1.5 wt %.

The experimental additive was dissolved in railway diesel crankcase lubricating oil and evaluated using the UPOT test.

The railway diesel crankcase lubricating oil consisted of a mixture of two components, a major component and a minor component. A description of each component is summarized below:

(a) a major portion of a liquid paraffinic mineral oil having a viscosity at 100° C. of about 52.5 SUS, at 100° C. of about 75.0 to 79.0 SUS and a liquid naphthenic mineral oil having a viscosity at 100° C. of about 75.0 to 80.0 SUS; and (b) a minor component of, as an oxidation and corrosion inhibiting agent, a condensate product prepared as mentioned earlier from the reaction of a oligomeric isobutylene, maleic anhydride, 2,5-dimercapto 1,3,4-thiadiazole, and an N-alkyl-alkylene diamine.

OIL OXIDATION TEST

The test method involves bubbling 5 liters of oxygen per hour through 300 mls of test oil composition at 285° F. in which there is immersed a 1"×3"×0.06 inch steel -backed copper-lead test specimen, cut from bearing stock. The viscosity of the test oil is measured before and after the 144 hour test period where the greater the differences between these two viscosities is indicative of higher oxidation levels. Moreover, the test specimen is weighed before and after the test period where the greater the weight loss the greater is the corrosion in the formulation. And, further, the larger the amount of copper, lead, and iron moieties found in the oil after the test, the greater the oxidation/corrosion deterioration thereof.

The representative Formulations A,B and comparative Formulation C and their oxidation test results are reported below in Table I.

TABLE I

Summary Of Union Pacific Oxidation Test Results After 144 Hours At 285° F.

| Composition, Wt % | UNTREATED (A) | TREATED (B) | TREATED (C) |
|---|---|---|---|
| SNO-20 | 5.00 | 5.00 | 5.00 |
| SNO-40 | 48.30 | 48.30 | 48.30 |
| 75/80 Pale Oil | 37.00 | 37.00 | 37.00 |
| PC-140* | 5.55 | 5.55 | 5.55 |
| TC-9596A** | 4.05 | 4.05 | 4.05 |
| Chlorowax 500° C. | 0.05 | 0.05 | 0.05 |
| TC-10314** | 0.05 | 0.05 | 0.05 |
| TX-1416*** | 150 | 150 | 1.50 |
| Experimental Additive | — | 1.00 | 2.00 |
| Union Pacific Oxidation Test | | | |
| Weight Loss. mg. | 280 | 3.1 | 2.0 |
| Viscosity Increase. %. | 160 | 67.0 | 59.0 |

*(PC-140) is a phenolic stabilizing agent:
**(TC-9596A and TC-10314) and
***(TX-1416) are. respectively. aromatic and dialiphatic - Mannich-base anti-oxidants: and all PC. TC and TX products are manufactured and sold by Texaco Chemical Company of Houston. Texas.

It is evident from the above results, that the incorporation of 1wt %, or 2wt. % of the oligomeric additive causes enhanced anti-oxidative and corrosive resistance to be imparted to the railway oil.

We claim:

1. A railway diesel crankcase lubricant composition comprising a major portion of a diesel lubricating oil and a minor amount of, as an oxidation and corrosion inhibiting agent, a condensate product prepared by the process comprising:

(a) reacting a dibasic acid anhydride of the formula:

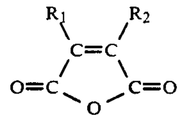

where $R_1$ and $R_2$ is hydrogen or a ($C_1C_{10}$) linear or branched alkyl or cyclic alkyl group, separately, with (i) an oligomeric isobutylene represented the formula;

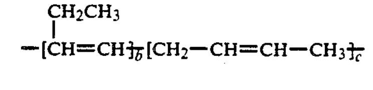

where the sum of the repeat units, b and c, are limited to the range of 10 to 500 so that the material has a corresponding molecular weight range from about 500 amu to 15,000 amu to produce oligomeric (isobutylene -g- succinic anhydride) and (ii) 2,5-dimercapto-1,3,4,- thiadiazole represented by the formula

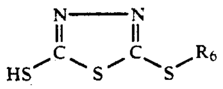

where $R_6$ is hydrogen or a ($C_1$–$C_{10}$) linear or branched aliphatic hydrocarbon, to produce 2-thio-(5-mercapto-1,3,4-thiadiazole) succinic anhydride;

(b) reacting said oligomeric (isobutylene-g-succinic anhydride) and said thiadiazole succinic anhydride with pentamethylenehexaamine to produce the [2-thio-(5-mercapto-1,3,4-thiadiazole)] -[oligomeric (isobutylene-g-succinic)] - pentamethylenetetramine-bis-succinimide; and (c) recovering said bis-succinimide product.

2. The railway diesel crankcase lubricant composition of claim 1, wherein said oligomeric isobutylene has a molecular weight (Mn) ranging from about 800 to about 2500 amu.

3. The railway diesel crankcase lubricant composition of claim 1, wherein said pentamethylenehexaamine is substituted with a N-alkyl alkylene diamine having the formula

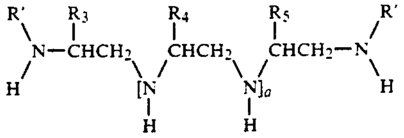

wherein R′ is hydrogen or a ($C_1$–$C_{10}$) hydrocarbon group and $R_3$, $R_4$, and $R_5$ each are hydrogen or a ($C_1$–$C_{10}$) hydrocarbon group, and a is an integer between 0 and 7.

4. The railway diesel crankcase lubricant composition of claim 1, wherein the minor amount of inhibiting agent ranges from about 0.01 wt % to about 15.0 wt % of said lubricant composition.

5. The railway diesel crankcase lubricant composition of claim 1, wherein the minor amount of inhibiting agent ranges from about 1.0 wt % to about 2.0 wt %.

* * * * *